US008065009B2

(12) United States Patent
Biggs

(10) Patent No.: US 8,065,009 B2
(45) Date of Patent: Nov. 22, 2011

(54) HEADER OVER-MOLDED ON A FEEDTHROUGH ASSEMBLY FOR AN IMPLANTABLE DEVICE

(75) Inventor: James C. Biggs, Plymouth, MN (US)

(73) Assignee: Greatbatch Ltd., Clarence, NY (US)

( * ) Notice: Subject to any disclaimer, the term of this patent is extended or adjusted under 35 U.S.C. 154(b) by 485 days.

(21) Appl. No.: 12/255,681

(22) Filed: Oct. 22, 2008

(65) Prior Publication Data
US 2009/0192578 A1    Jul. 30, 2009

Related U.S. Application Data

(60) Provisional application No. 61/023,624, filed on Jan. 25, 2008.

(51) Int. Cl.
*A61N 1/375* (2006.01)
(52) U.S. Cl. ........................................................ 607/37
(58) Field of Classification Search ...................... 607/37
See application file for complete search history.

(56) References Cited

U.S. PATENT DOCUMENTS

| 5,755,743 | A | * | 5/1998 | Volz et al. ........................ 607/37 |
| 7,069,081 | B2 | | 6/2006 | Biggs et al. |
| 7,167,749 | B2 | | 1/2007 | Biggs et al. |
| 7,747,321 | B2 | * | 6/2010 | Fischbach et al. .............. 607/36 |
| 2004/0023109 | A1 | | 2/2004 | Rusin et al. |
| 2005/0060003 | A1 | * | 3/2005 | Taylor et al. .................... 607/36 |
| 2006/0047321 | A1 | | 3/2006 | Biggs et al. |

* cited by examiner

*Primary Examiner* — Kennedy Schaetzle
(74) *Attorney, Agent, or Firm* — Michael F. Scalise

(57) ABSTRACT

A header assembly for connecting a conductor terminating at a body organ with an implantable medical device is described. The header assembly comprises a base plate, a feedthrough subassembly disposed in the base plate and comprising a ceramic-to-metal seal with first and second feedthrough wires passing through the ceramic-to-metal seal; a first electrically conductive terminal connected to a distal end of the first feedthrough wire and having a first lead opening sized to receive a first portion of a lead for the conductor; a second electrically conductive terminal connected to a distal end of the second feedthrough wire and having a second lead opening sized to receive a second portion of the lead for the conductor; a body of polymeric material molded in a two-part construction to encase the conductive terminals and their feedthrough wires except for a first bore communicating from outside the polymeric body to the first and second lead openings aligned in a first co-axial relationship. Preferably, the polymeric body comprises a first polymeric material such as Techothane® or Polysulfone® encasing the terminals except the bore and an epoxy as a second polymeric material molded over the first polymeric material.

38 Claims, 14 Drawing Sheets

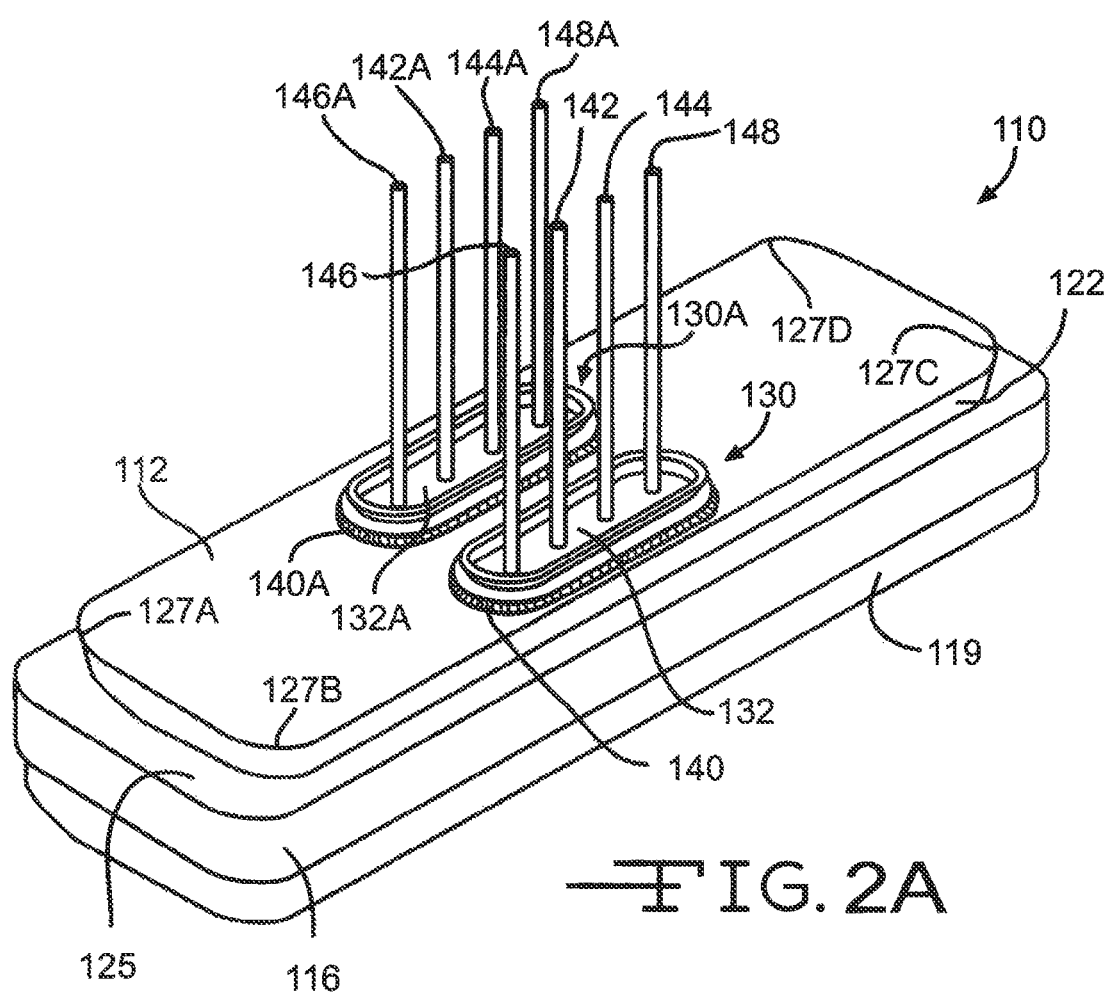

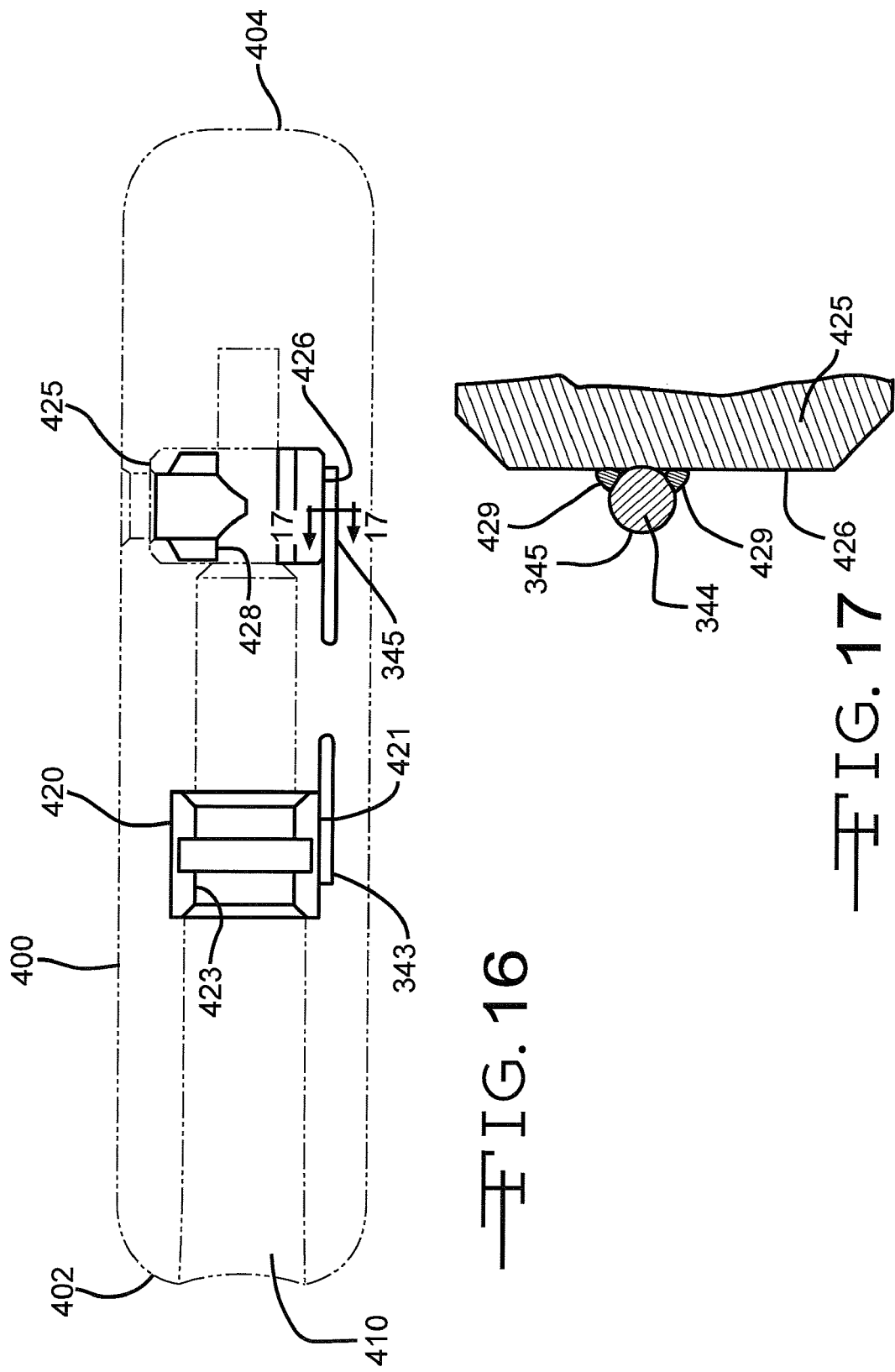

HEADER OVER-MOLDED ON A FEEDTHROUGH ASSEMBLY FOR AN IMPLANTABLE DEVICE

CROSS-REFERENCE TO RELATED APPLICATION

This application claims priority from U.S. provisional Application Ser. No. 61/023,624, filed Jan. 25, 2008.

BACKGROUND OF THE INVENTION

1. Field of the Invention

The invention relates to a one-piece header assembly for connecting an implantable medical device to a body organ intended to be assisted by the medical device. The header assembly includes a feedthrough assembly that is hermetically welded onto a base plate, which is subsequently welded to the medical device.

2. Description of Related Art

Header assemblies for implantable medical devices generally comprise feedthrough conductors in the form of pins or wires connected to the internal components of the medical device. The feedthrough wires extend through a wall of the medical device housing, such as a lid, and are electrically insulated there from by a ceramic-to-metal seal, and the like. Electrical continuity is established by connecting intermediate conductor wires between the feedthrough wires and connector blocks in the header assembly. Examples of this type of header assembly are shown in U.S. Pat. No. 4,254,775 to Langer, U.S. Pat. No. 4,262,673 to Kinney et al., U.S. Pat. No. 4,764,132 to Stutz, Jr., U.S. Pat. No. 5,282,841 to Szyszkowski and U.S. Pat. No. 5,336,246 to Dantanarayana, the disclosures of which are incorporated herein by reference. The intermediate conductor wires of the implantable medical devices disclosed in these patents represent electrical connections that could fail through improper connection, corrosion, breakage, and the like.

More recently, U.S. Pat. No. 7,069,081 to Biggs et al., which is assigned to the assignee of the present invention and incorporated herein by reference, describes a header assembly attachable to a medical device for the purpose of connecting its output terminals to at least one lead, the lead terminating at a target organ or portion of the body intending to be assisted. A number of leads are connectable to the header, including single and coaxial leads. The header assembly may be molded directly to the medical device or preformed and then attached to the device casing, either by mechanical fasteners and/or chemical adhesive.

These header assemblies require either a backfilled liquid sealing material to be dispensed between the bottom side of the header assembly and the upper lid of the implantable device, or complex mechanical fasteners to firmly secure the header assembly to the device, or both. These features increase device cost and manufacturing cycle time, while the sealing connection between the header assembly and the device is still less reliable than desired.

Accordingly, there remains a need for a header assembly that can be quickly and simply manufactured, and that can be joined to an implantable device in a long lasting hermetic seal without sealant backfilling or complex fasteners.

SUMMARY OF THE INVENTION

Embodiments of the present invention are therefore provided that meet at least one or more of the following objects of the present invention.

It is an object of this invention to provide a header assembly for an implantable medical device that has improved sealing to the device.

It is a further object of this invention to provide a header assembly for an implantable medical device that can be more quickly and easily manufactured than currently known for prior art designs.

According to the present invention, a header assembly for connecting a conductor terminating at a body organ with control circuitry and at least one electrical energy storage device of an implantable medical device is provided. The header assembly comprises a base plate comprising an upper surface, a lower surface, and a surrounding edge, the surrounding edge having a lower region and an upper region comprising an overhang having a lower perimeter and an upper perimeter, wherein the upper perimeter is greater than the lower perimeter; a first feedthrough subassembly disposed in a first through hole in the base plate, the first feedthrough subassembly comprising a first ceramic-to-metal seal formed within the first through hole, and a first feedthrough wire and a second feedthrough wire passing through the first ceramic-to-metal seal; a first electrically conductive terminal connected to a distal end of the first feedthrough wire and having a first lead opening sized to receive a first portion of a lead for the conductor; a second electrically conductive terminal connected to a distal end of the second feedthrough wire and having a second lead opening sized to receive a second portion of the lead for the conductor; a body of polymeric material molded as a single piece to encase the upper region of the surrounding edge of the base plate and to support the first and second terminals in a partially encased relationship so that the first and second terminals are prevented from moving by the polymeric material; and a first bore communicating from outside the polymeric body to the first and second lead openings aligned in a first co-axial relationship.

The upper region of the base plate is preferably dovetail shaped, thereby enabling it to anchor into the polymeric body securely and provide a superior seal of the polymeric body to the base plate. The polymeric body is preferably molded from polyurethane or polysulfone, each of which shrink slightly during curing in the mold. The shrinkage results in a constricting force being applied to the dovetail shaped upper region of the surrounding edge of the base plate, thereby providing the improved seal of the polymeric body to the base plate. The base plate is preferably made from the same material as the implantable device casing, such as stainless steel or titanium.

In one embodiment, the first feedthrough subassembly further comprises a first tubular body having a main body perimeter, an inner bore containing the first ceramic-to-metal seal, and a upper end with a upper perimeter greater than the tubular main body perimeter. The upper end of the first tubular body is preferably dovetail shaped, thereby providing additional anchoring of the feedthrough subassembly into the molded polymeric body and a superior seal therewith. The tubular body of the feedthrough subassembly may be formed integrally with the base plate, or as a separate piece. If the tubular body is formed separately, it is preferably joined and hermetically sealed to the base plate by welding. A separate tubular body may also be provided with a flange that is proximate to the upper end thereof and engaged with the upper surface of the base plate.

The header assembly may be provided with only the first bore in the molded polymeric body for accepting a lead of a conductor terminating at a body organ, or the molded polymeric body may include additional bores. In one embodiment, the molded polymeric body is provided with two such bores, wherein the molded polymeric body further supports third and fourth electrically conductive terminals having third and fourth lead openings aligned in a second co-axial relationship along the second bore communicating from outside the body to the third and fourth terminals.

The additional third and fourth feedthrough wires connected to the third and fourth terminals may be formed as part of the first feedthrough subassembly. In this embodiment, the first feedthrough subassembly further comprises a third feedthrough wire having a distal end connected to the third electrically conductive terminal and passing through the first ceramic-to-metal seal, and a fourth feedthrough wire having a distal end connected to the fourth electrically conductive terminal and passing through the first ceramic-to-metal seal. The additional third and fourth lead openings of the third and fourth terminals are aligned in a co-axial relationship. The co-axial relationship of the third and fourth terminals is parallel to the co-axial relationship of the first and second terminals.

Alternatively, the additional third and fourth feedthrough wires connected to the third and fourth terminals may be formed as part of a second feedthrough subassembly. In this embodiment, the second feedthrough subassembly is disposed in a second through hole in the base plate, and comprises a second ceramic-to-metal seal formed within the second through hole, a third feedthrough wire having a distal end connected to the third electrically conductive terminal and passing through the second ceramic-to-metal seal, and a fourth feedthrough wire having a distal end connected to the fourth electrically conductive terminal and passing through the second ceramic-to-metal seal. The additional third and fourth lead openings of the third and fourth terminals are aligned in a co-axial relationship. The co-axial relationship of the third and fourth terminals is parallel to the co-axial relationship of the first and second terminals. The second feedthrough subassembly may include a tubular body with a dovetail structure and/or a flange, and may be welded to the base plate, as described previously for the first feedthrough assembly.

Also according to the present invention, a header assembly for connecting at least the first and second conductors terminating at a body organ with control circuitry and at least one electrical energy storage device of an implantable medical device is provided. The header assembly comprises a base plate comprising an upper surface, a lower surface, and a surrounding edge, the surrounding edge having a lower region and an upper region; a first feedthrough subassembly disposed in a first through hole in the base plate, the first feedthrough subassembly comprising a first ceramic-to-metal seal formed within the first through hole, and a first feedthrough wire and a second feedthrough wire passing through the first ceramic-to-metal seal; a second feedthrough subassembly disposed in a second through hole in the base plate, the second feedthrough subassembly comprising a second ceramic-to-metal seal formed within the second through hole, and a third feedthrough wire and a fourth feedthrough wire passing through the second ceramic-to-metal seal; a first electrically conductive terminal connected to a distal end of the first feedthrough wire and having a first lead opening sized to receive a first portion of a lead for the first conductor; a second electrically conductive terminal connected to a distal end of the second feedthrough wire and having a second lead opening sized to receive a first portion of the lead for the second conductor; a third electrically conductive terminal connected to a distal end of the third feedthrough wire and having a third lead opening sized to receive a second portion of a lead for the first conductor; a fourth electrically conductive terminal connected to a distal end of the fourth feedthrough wire and having a fourth lead opening sized to receive a second portion of the lead for the second conductor; a body of polymeric material molded as a single, monolithic piece to support the first, second, third, and fourth terminals in a partially encased relationship so that the first, second, third, and fourth terminals are prevented from moving by the polymeric material; a first bore communicating from outside the polymeric body to the first and third lead openings aligned in a first co-axial relationship; and a second bore communicating from outside the polymeric body to the second and fourth lead openings aligned in a second co-axial relationship.

The feedthrough subassembly or assemblies may be positioned with respect to the conductive terminals so as to simplify the bending and routing of the feedthrough wires between them. In one embodiment, the feedthrough wires may be aligned substantially perpendicular to the lead openings of their respective terminals. The feedthrough wires may be disposed in grooves formed on the exterior surfaces of the terminals, thereby enabling more precise positioning and stronger welding of the wires to the terminals.

The upper region of the surrounding edge of the base plate may comprise an overhang that may be dovetail shaped as previously described. The feedthrough assemblies may be comprised of tubular bodies containing the ceramic-to-metal seals, and the tubular bodies may include an overhang and/or a flange. The tubular bodies are preferably joined to the base plate by welding.

Also according to the present invention, an implantable device is provided comprising a casing, at least one electrical energy storage device contained in the casing; control circuitry contained in the casing; and a header assembly. The header assembly comprises a base plate comprising an upper surface, a lower surface, and a surrounding edge, the surrounding edge having a lower region and an upper region comprising an overhang having a lower perimeter and an upper perimeter, wherein the upper perimeter is greater than the lower perimeter; a first feedthrough subassembly disposed in a first through hole in the base plate, the first feedthrough subassembly comprising a first ceramic-to-metal seal formed within the first through hole, and a first feedthrough wire and a second feedthrough wire passing through the first ceramic-to-metal seal; a first electrically conductive terminal connected to a distal end of the first feedthrough wire and having a first lead opening sized to receive a first portion of a lead for the conductor; a second electrically conductive terminal connected to a distal end of the second feedthrough wire and having a second lead opening sized to receive a second portion of the lead for the conductor; a body of polymeric material molded as a single piece to encase the upper region of the surrounding edge of the base plate and to support the first and second terminals in a partially encased relationship so that the first and second terminals are prevented from moving by the polymeric material; and a first bore communicating from outside the polymeric body to the first and second lead openings aligned in a first co-axial relationship.

Alternatively, the header assembly of the implantable device may be comprised of a base plate comprising an upper surface, a lower surface, and a surrounding edge, the surrounding edge having a lower region and an upper region; a first feedthrough subassembly disposed in a first through hole in the base plate, the first feedthrough subassembly comprising a first ceramic-to-metal seal formed within the first through hole, and a first feedthrough wire and a second feedthrough wire passing through the first ceramic-to-metal seal; a second feedthrough subassembly disposed in a second through hole in the base plate, the second feedthrough subassembly comprising a second ceramic-to-metal seal formed within the second through hole, and a third feedthrough wire and a fourth feedthrough wire passing through the second ceramic-to-metal seal; a first electrically conductive terminal connected to a distal end of the first feedthrough wire and having a first lead opening sized to receive a first portion of a lead for the first conductor; a second electrically conductive terminal connected to a distal end of the second feedthrough wire and having a second lead opening sized to receive a first portion of the lead for the second conductor; a third electrically conductive terminal connected to a distal end of the third feedthrough wire and having a third lead opening sized to receive a second portion of a lead for the first conductor; a fourth electrically conductive terminal connected to a distal end of the fourth feedthrough wire and having a fourth lead opening sized to receive a second portion of the lead for the second conductor; a body of polymeric material molded as a single piece to support the first, second, third, and fourth terminals in a partially encased relationship so that the first, second, third, and fourth terminals are prevented from moving by the polymeric material; a first bore communicating from outside the polymeric body to the first and third lead openings aligned in a first co-axial relationship; and a second bore communicating from outside the polymeric body to the second and fourth lead openings aligned in a second co-axial relationship.

The foregoing and additional objects, advantages, and characterizing features of the present invention will become increasingly more apparent upon a reading of the following detailed description together with the included drawings.

BRIEF DESCRIPTION OF THE DRAWINGS

The present invention will be described by reference to the following drawings, in which like numerals refer to like elements, and in which:

FIG. 2A is a perspective view of a base plate and feedthrough subassembly of another embodiment of the header assembly;

FIG. 16 is a cross-sectional view taken along the line 16-16 of FIG. 12; and

FIG. 17 is a cross-sectional view taken along line 17-17 of FIG. 16.

The present invention will be described in connection with preferred embodiments, however, it will be understood that there is no intent to limit the invention to the embodiments described. On the contrary, the intent is to cover all alternatives, modifications, and equivalents as may be included within the scope of the invention as defined by the appended claims.

DETAILED DESCRIPTION OF THE PREFERRED EMBODIMENTS

Figure 1:
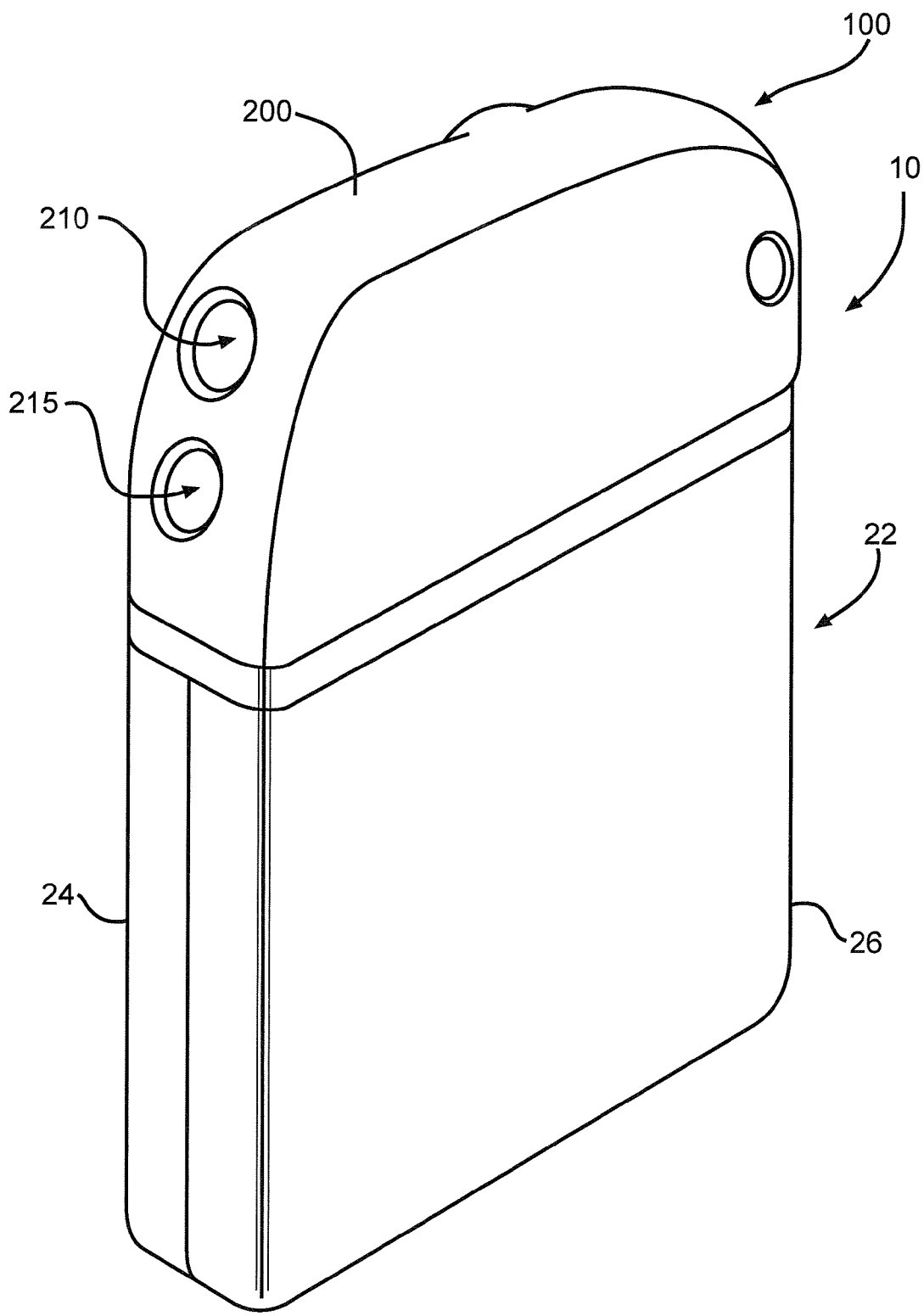
FIG. 1 is a perspective view of an implantable medical device including a header assembly of the present invention.
Figure 10:
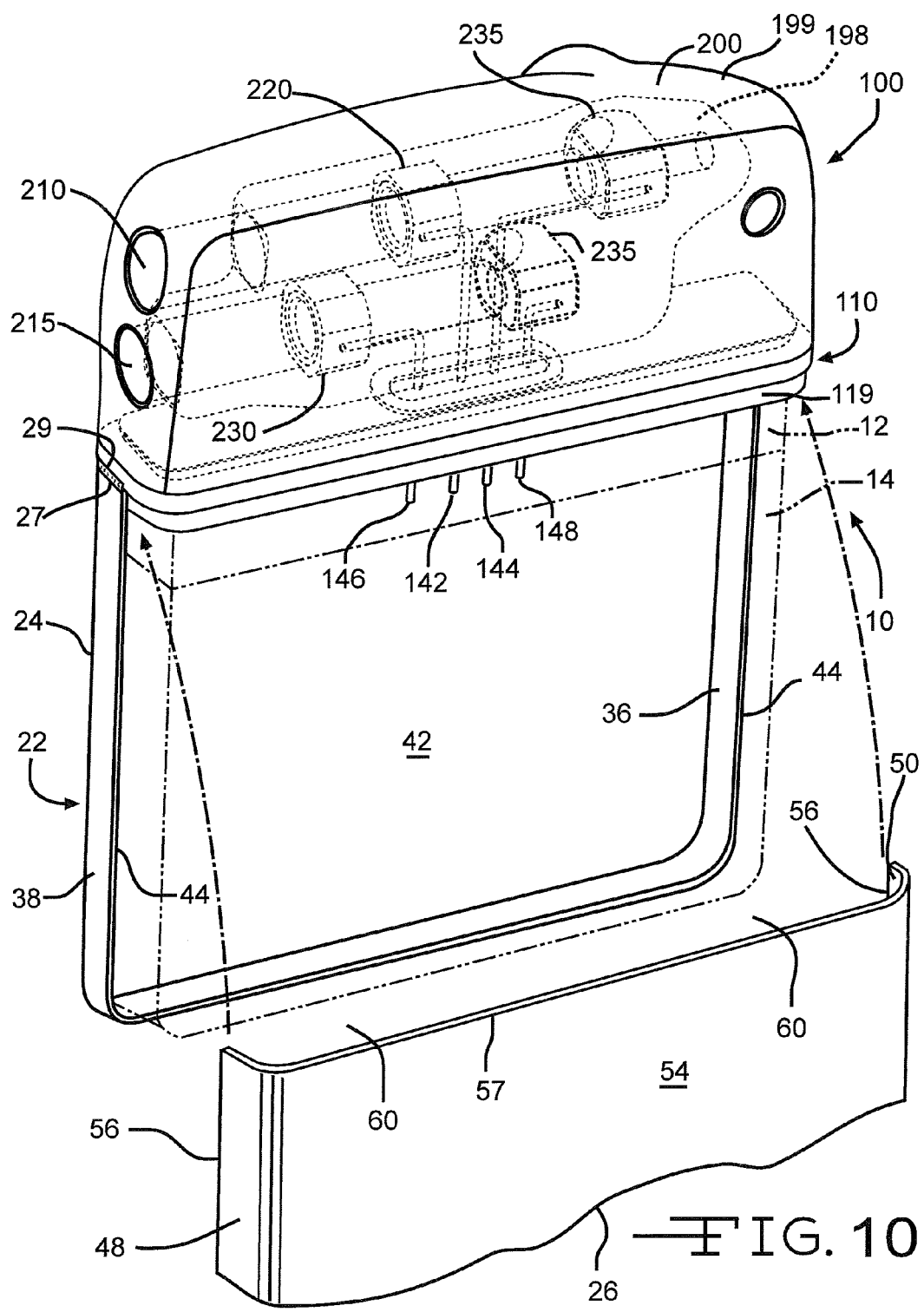
FIG. 10 is a perspective view of the header assembly of FIG. 9 partially joined to a clamshell device casing.

Turning now to the drawings, FIG. 1 is a perspective view of an implantable medical device 10 including a header assembly 100 of the present invention. FIG. 10 is a similar view of the header assembly 100 with one half of the clamshells comprising the device casing having been removed. The implantable medical device 10 is exemplary of any one of a number of known assist devices such as cardiac defibrillators, cardiac pacemakers, drug pumps, neurostimulators, hearing assist devices, and the like.

The implantable medical device 10 is contained in a housing 22 of a material such as of stainless steel, and is shown in an exemplary form comprising first and second main clam shell portions 24 and 26. The clam shells 24 and 26 are mated together and hermetically sealed about their periphery to provide an enclosure for the medical device 10. The medical device further comprises control circuitry 12 (FIG. 11) and a power supply 14 such as a battery. The battery is connected to the control circuitry by electrical leads. There may also be a capacitor for a medical device such as a defibrillator. Details of an exemplary implantable medical device comprising a clamshell-type housing are shown in the aforementioned U.S. Pat. No. 7,069,081 to Biggs et al. and will thus not be provided here.

Figure 2:
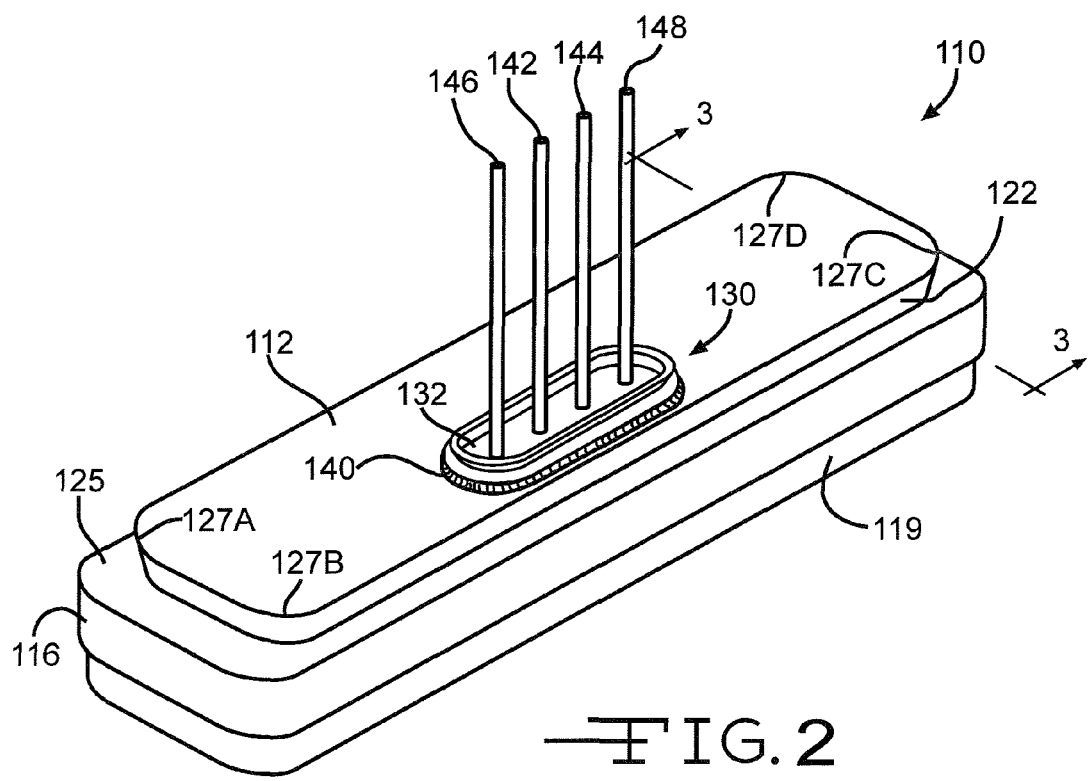
FIG. 2 is a perspective view of a base plate and feedthrough subassembly of one embodiment of the header assembly.
Figure 3:
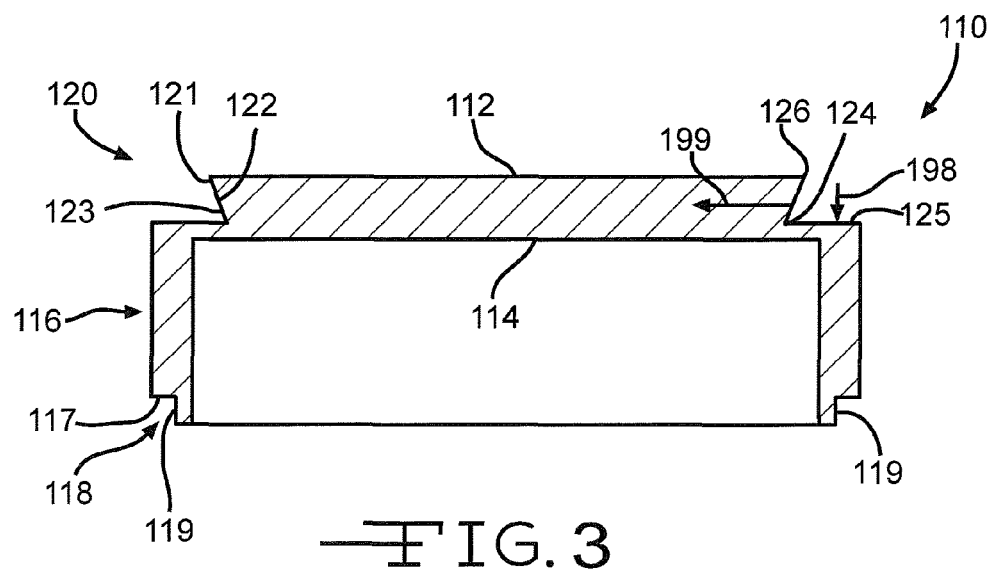
FIG. 3 is a cross sectional view taken along line 3-3 of FIG. 2.

Referring now to FIGS. 2 and 3, a base plate and feedthrough subassembly for one embodiment of the header assembly are shown. Base plate 110 functions as a lid, being sealed to the device casing 22 housing the implantable device 10 therein in the same manner as described in the '081 patent of Biggs et al. Additionally, base plate 110 functions as a structure to which the body of polymeric material is joined and sealed without the use of separate fasteners and/or adhesives. This latter aspect of the invention will be described in detail hereinafter.

Base plate 110 has an overall shape corresponding to the upper opening of device casing 22, and is typically rectangular in shape with curved or rounded corners. Base plate 110 comprises an upper surface 112, a lower surface 114, and a surrounding edge 116. Surrounding edge 116 includes a lower region 118 and an upper region 120.

Both the lower and upper regions 118, 120 of the surrounding edge 116 are preferably provided with specialized structures to improve sealing and reliability of the implantable device 10. Referring also to FIG. 3, the lower region 118 of the surrounding edge 116 includes an inverted step or rim 119 to assist in the sealing connection between the base plate 110 and the mated clam shells 24, 26. Preferably, the base plate 110 is sealed in place, such as by laser welding (not shown), to create the hermetic housing 22 for the implantable medical device 18.

The upper region 120 of the surrounding edge 116 includes an overhang 122, the upper portion 121 of which has a greater perimeter than the lower portion 123. It will be apparent that overhang 122 may be provided in a variety of shapes in which the upper portion 121 is of a greater perimeter than the lower portion 123. For example, overhang 122 may be tee-shaped. In the preferred embodiment depicted in FIGS. 2 and 3, overhang 122 is dovetail-shaped. The dovetail shape is formed by the adjacent acute angles 124 and 126. Acute angle 124 is formed at the intersection of shoulder 125 and lower portion 123. The acute angle 126 is formed at the intersection of upper portion 121 and upper surface 112. Thus, when the polymeric body 200 of the header assembly 100 is molded over base plate 110 (as will be described subsequently herein) the overhang 122 is embedded therein and serves to anchor the base plate 110 within the polymeric body and to resist forces that could otherwise separate them from each other.

Figure 4:
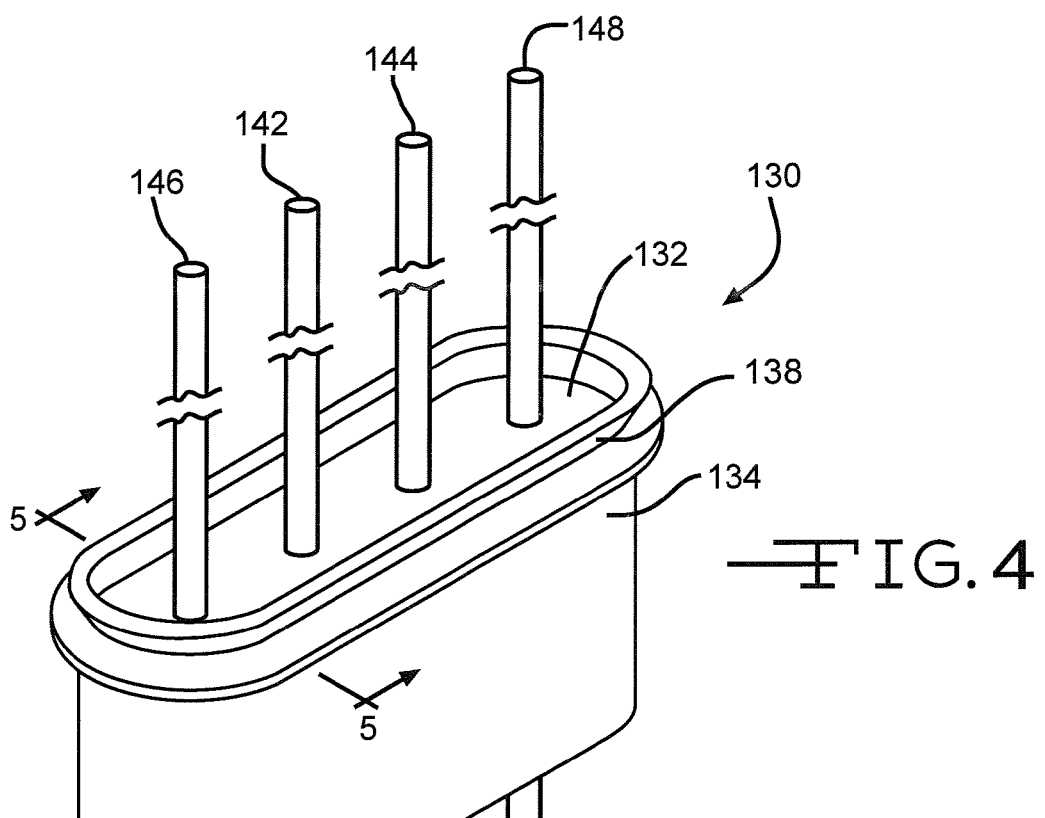
FIG. 4 is a perspective view of the feedthrough subassembly of FIG. 2, prior to joining to the base plate.
Figure 5:
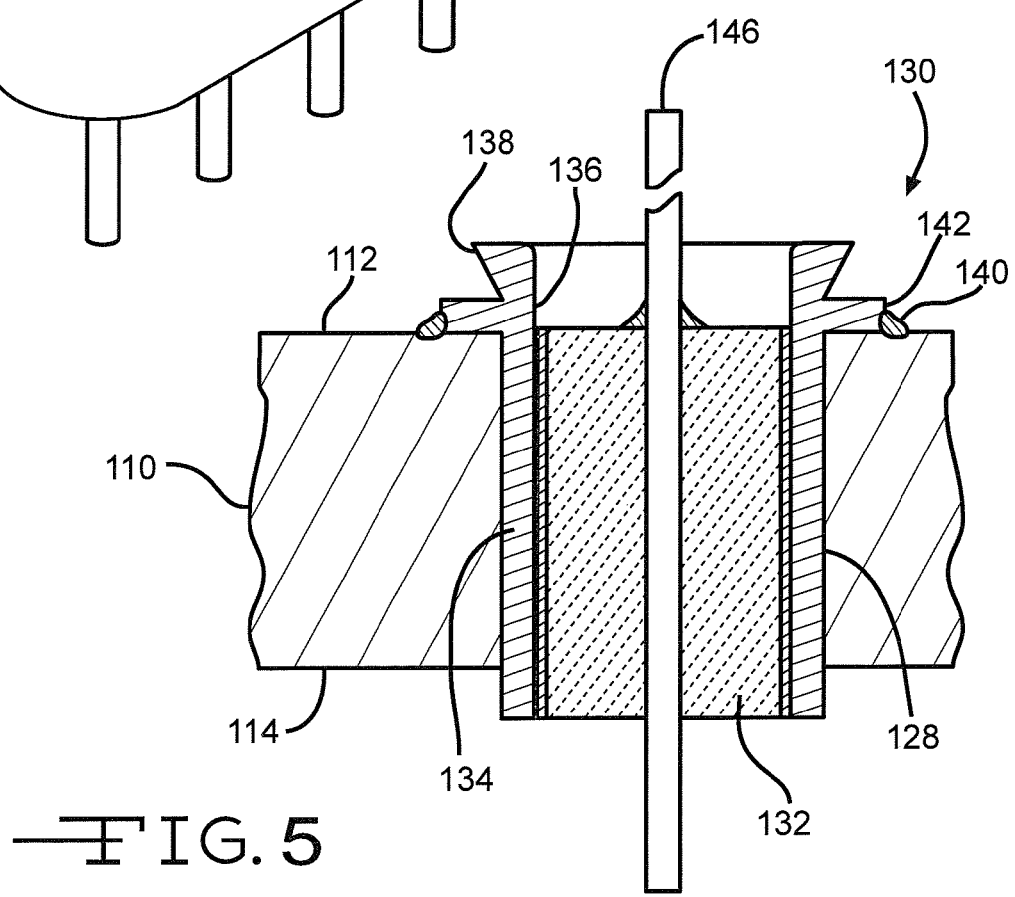
FIG. 5 is a cross sectional view taken along the line 5-5 of FIG. 4.

Referring now to FIGS. 2, 4, and 5, the header assembly 100 further comprises a first feedthrough subassembly 130 disposed in a first through hole 128 in the base plate 110. First feedthrough subassembly 130 includes a first ceramic-to-metal seal 132 formed within the first through hole 128. A first feedthrough wire 142 and a second feedthrough wire 144 pass through the first ceramic-to-metal seal 132 and are connected to conductive terminals, which in turn may be connected to a conductive lead to be plugged into the header assembly, as will be explained subsequently.

In the header assembly 100 of FIGS. 1 and 9 to 11, two bores 210, 215 and four conductive terminals 220, 225, 230 and 235 are provided for receiving and connecting two conductive leads (not shown) into the header assembly. Thus, in the first feedthrough subassembly 130 of FIGS. 2, 4 and 5, four feedthrough wires 142, 144, 146 and 148 are provided for connecting to the respective pairs of conductive terminals 220, 225 and 230, 235.

An alternate embodiment of a header assembly 110 is illustrated in FIG. 2A comprising the first feedthrough subassembly 130 side-by-side with a second feedthrough subassembly 130A. The second feedthrough subassembly 130A has a second ceramic-to-metal seal 132A that is sealed to the base plate by weld 140A. The second ceramic-to-metal seal 132A supports four feedthrough wires 142A, 144A, 146A and 148A for connecting to the respective second pairs of conductive terminals (not shown).

The feedthrough subassembly may be either formed integrally with the base plate, or as a separate part which is joined to the base plate. The latter embodiment is depicted in FIGS. 2, 4, and 5. The first feedthrough subassembly 130 further comprises a first tubular body 134 having a main body perimeter, an inner bore 136 containing the first ceramic-to-metal seal 132, and a feedthrough overhang 138 with an upper perimeter greater than the tubular main body perimeter. The feedthrough overhang 138 provided for strong engagement with the molded polymer body in a similar manner as the overhang 122 of the base plate 110, as will be described hereinafter. The feedthrough overhang 138 is preferably dovetail shaped, thereby providing firm anchoring of the feedthrough subassembly into the molded polymeric body and a superior seal therewith via a constricting force as will be described in detail presently. The tubular body 134 is joined and hermetically sealed to base plate 110 by weld 140. The tubular body 134 may also be provided with a flange 142 that is proximate to the upper end thereof and engaged with the upper surface 112 of the base plate 110. The tubular body 134 is preferably provided with an oblong shape with a length as needed to accommodate the number of feedthrough wires disposed in the ceramic-to-metal seal therein.

Figure 15:
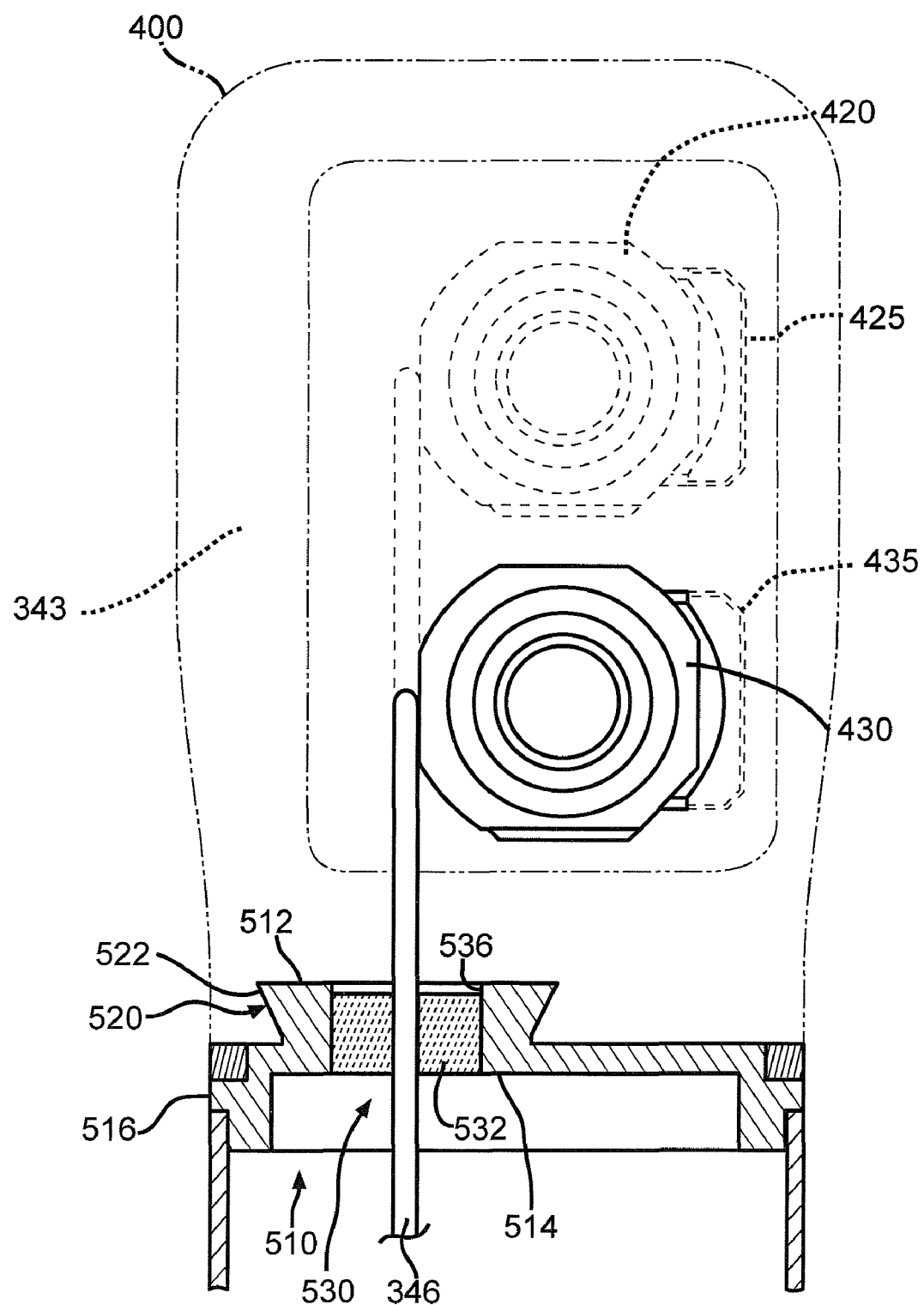
FIG. 15 is a an alternative embodiment of the header assembly of FIG. 14, wherein the feedthrough subassembly is formed integrally with the base plate of the header assembly.

FIG. 15 depicts an alternative base plate 510 comprising an upper surface 512, a lower surface 514, and a surrounding edge 516. The upper region 520 of the surrounding edge 516 includes an overhang 522 preferably having a dovetail shape as described previously for base plate 110 of FIG. 3. The feedthrough subassembly 530 is formed integrally within base plate 510, with ceramic-to-metal seal 532 and feedthrough wires 346 and 342 (FIG. 13) contained within the inner bore 536 thereof.

Figure 6:
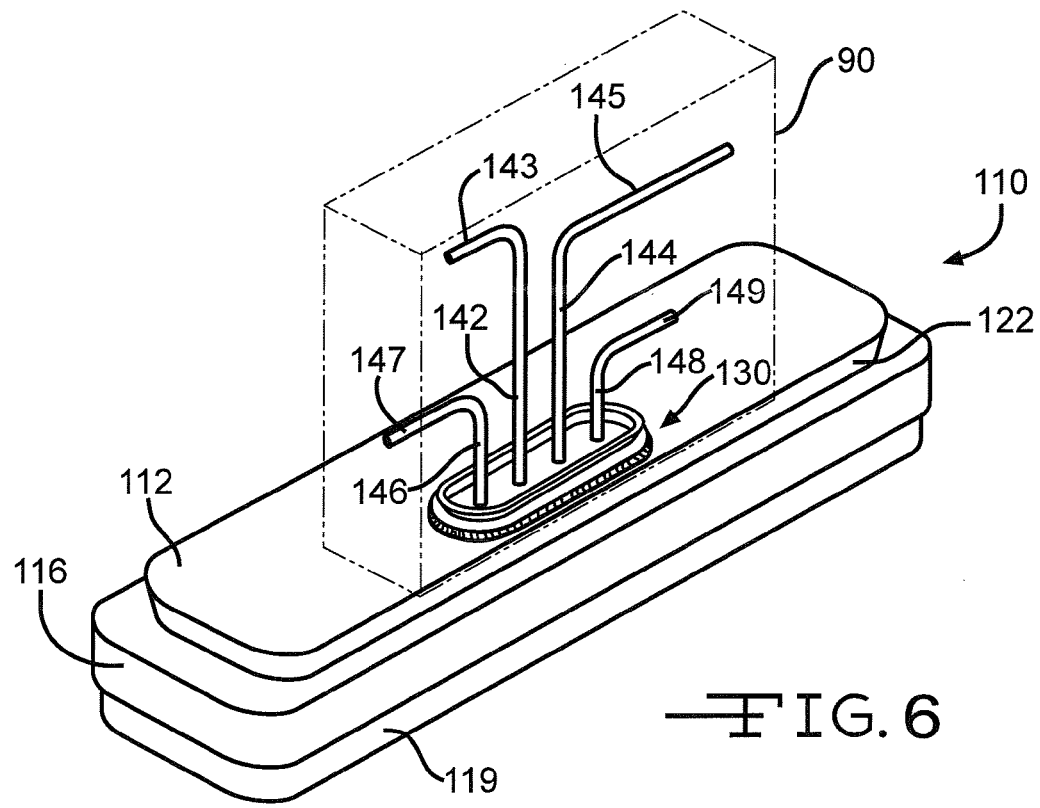
FIG. 6 is a perspective view of the base plate and feedthrough subassembly of FIG. 2, after forming of the wires of the feedthrough subassembly.
Figure 8:
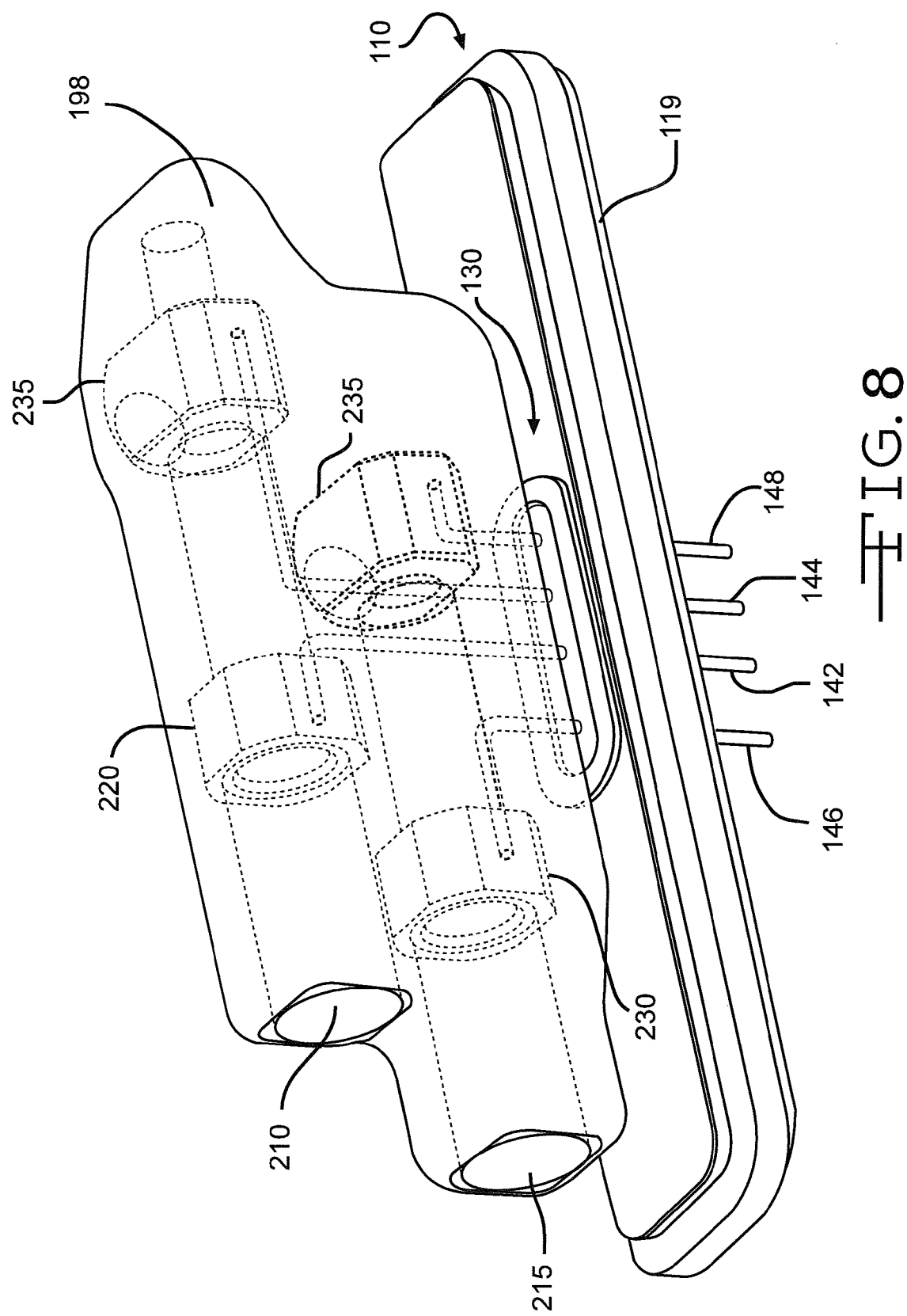
FIG. 8 is a perspective view showing the feedthrough subassembly of FIG. 7 partially encased in a first polymeric material.
Figure 9:
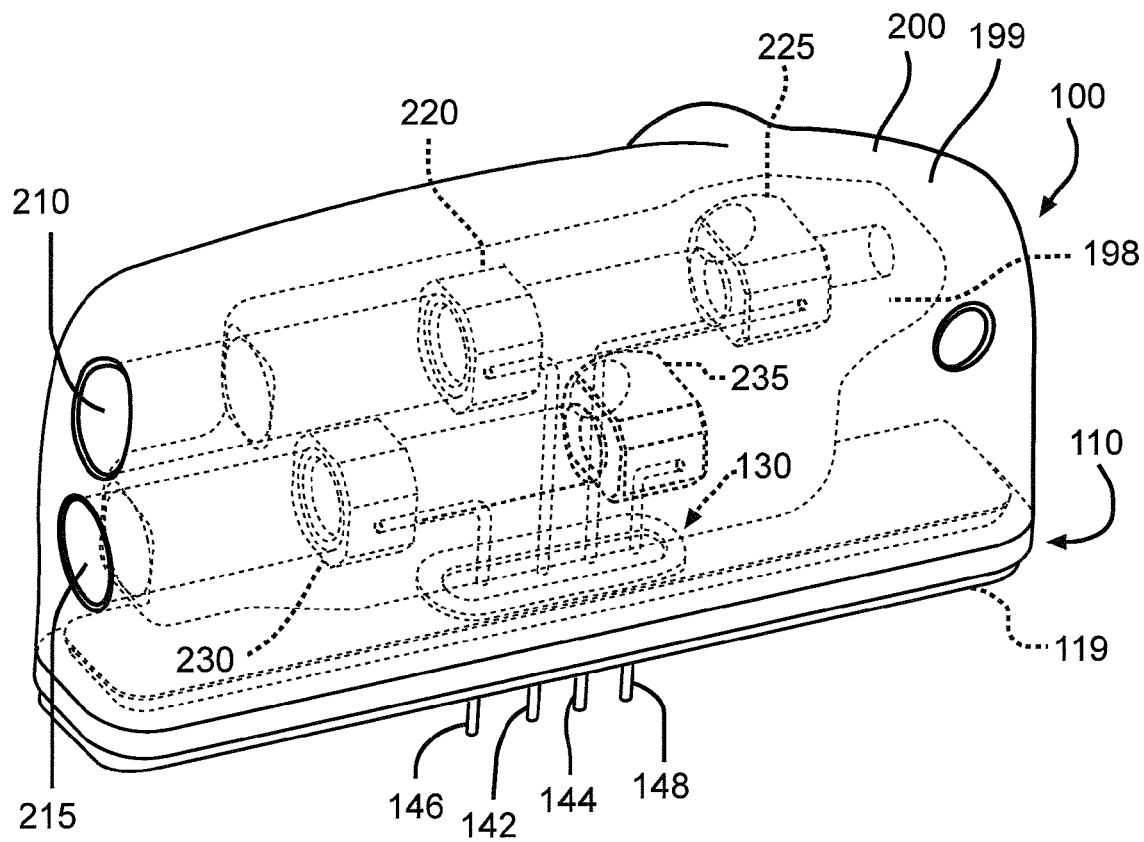
FIG. 9 is a perspective view of the molded header assembly including a base plate and a polymer body encasing the feedthrough assembly, wires, and terminal blocks.

Returning back to FIGS. 2 to 5, after the feedthrough subassembly 130 is supported in the base plate 110, the feedthrough wires 142, 144, 146 and 148 are bent into the required shapes and connected to the respective conductive terminals 220, 225, 230 and 235 prior to molding of the polymeric body as depicted in FIGS. 8 and 9. With the feedthrough wires 142, 144, 146 and 148 extending upwardly as shown in FIG. 4, a fixture and tool 90 (FIG. 6) is used to bend each of the distal ends 143, 145, 147 and 149 of the feedthrough wires into a desired position for later connection to the conductive terminals 220, 225, 230 and 235. Completion of this connection forms the feedthrough subassembly 130.

As shown in FIG. 8, after the feedthrough subassembly 130 is built, it is subjected to a first molding operation. This is where a first polymeric material 198, preferably of Techothane® or Polysulfone® is used to encase the terminals 220, 225, 230 and 235 except for bores 210A and 215A that are aligned with the openings 221, 226 and 231, 236 in the terminal pairs. The first polymeric material 198 also partially encasing the feedthrough wires 142, 144, 146 and 148 where they connect to the respective terminals 220, 225, 230 and 235, but not where they pass through the ceramic-to-metal seal 132.

The first polymeric material 198 is subsequently encased in a second polymeric material 199, which is preferably an epoxy. The second polymeric material 199 completely surrounds the first polymeric material 198 except the bores 210 and 215, which now have their final length. This means that the second polymeric material 199 encases the feedthrough wires 142, 144, 146 and 148 where they exit seal 132.

The previously described base plate overhang 122 is advantageous in providing a superior seal of the molded polymer body, particularly the second polymeric material 199, to the base plate 110. When the molded polymer 199 cures (and possibly cross links with the first polymeric material 198), a slight shrinkage occurs. This results in a constricting force of the second polymeric material 199 comprising the polymer body 200 against the dovetail as indicated by arrow 199. The constricting force against the angled surface of the dovetailed overhang 122 also results in a compressive force of the polymer body against the shoulder 125 of the base plate 110, as indicated by arrow 198. Thus, shrinkage of the second polymeric material 199 during curing results in a forced fit against the dovetail overhang 122 providing a superior seal of the polymer body 200 to the base plate 110. An additional advantageous feature of the overhang structure is that each of the corners 127A to 127D are radiused in order to avoid stress concentrations that might otherwise cause cracking of the polymer body if sharp corners were present. The molded polymer body 200 of header assembly 100 is made by suitable molding processes known in the art. For example, one may use a book molding process as described in U.S. Pat. No. 7,069,081 of Biggs et al.

The header assembly may be provided with only a first bore in the molded polymer body 200 for accepting a conductor lead terminating at a body organ, or it may include additional bores. In an embodiment wherein the header assembly 100 is provided with only a first bore in the polymeric body 200 for accepting a single lead, only two conductive terminals are provided. The first electrically conductive terminal 220 is connected to the distal end 143 of the first feedthrough wire 142 and the second electrically conductive terminal 225 is connected to the distal end 145 of the second feedthrough wire 144.

Conductive terminal 220 has a first lead opening 221 sized to receive a first portion of the conductor lead and conductive terminal 225 has a second lead opening 226 sized to receive a second portion of the lead. The lead and conductor terminating at a body organ are not shown herein. However, an exemplary conductor lead is shown in the aforementioned U.S. Pat. No. 7,069,081 to Biggs et al.

Figure 7:
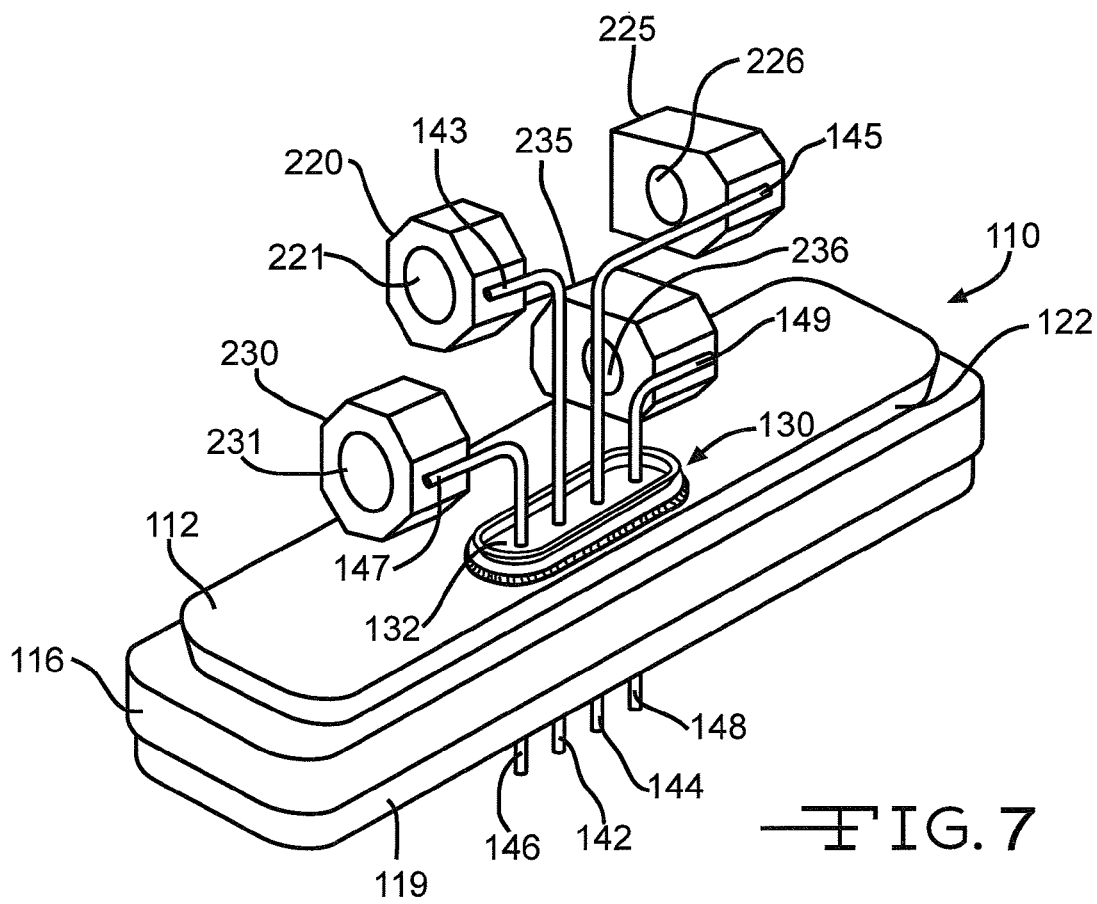
FIG. 7 is a perspective view of the base plate and feedthrough subassembly of FIG. 6, after the joining of terminal blocks to the ends of the wires of the feedthrough subassembly.

In the embodiment of the header assembly 100 depicted in FIGS. 1 to 11, the molded polymer body 200 is provided with two bores 210, 215 for receiving conductor leads. Four conductive terminals 220, 225, 230 and 235 are connected to the respective feedthrough wires 142, 144, 146 and 148, as shown in FIG. 7. The third terminal 230 is connected to the distal end 147 of the third feedthrough wire 146 and the fourth terminal 235 is connected to the distal end 149 of the fourth feedthrough wire 148. Conductive terminal 230 has a third lead opening 231 sized to receive a first portion of a second conductor lead and conductive terminal 235 has a fourth lead opening 236 sized to receive a second portion of the lead. The first lead opening 221 of the first terminal 220 and the second lead opening 226 of the second terminal 225 are aligned in a first coaxial relationship while the third lead opening 231 of the third terminal 230 and the fourth lead opening 236 of the fourth terminal 235 are aligned in a second coaxial relationship. This co-axial alignment is necessary for receiving the respective first and second conductor lead (not shown) in the bores 210, 215.

As shown in FIG. 7, the additional third and fourth feedthrough wires 146 and 148 connected to the respective third and fourth terminals 230 and 235 may be formed as part of the first feedthrough subassembly. In this embodiment, the first feedthrough subassembly 130 further comprises the third and fourth feedthrough wires 146 and 148 passing through the first ceramic-to-metal seal 132.

Figure 12:
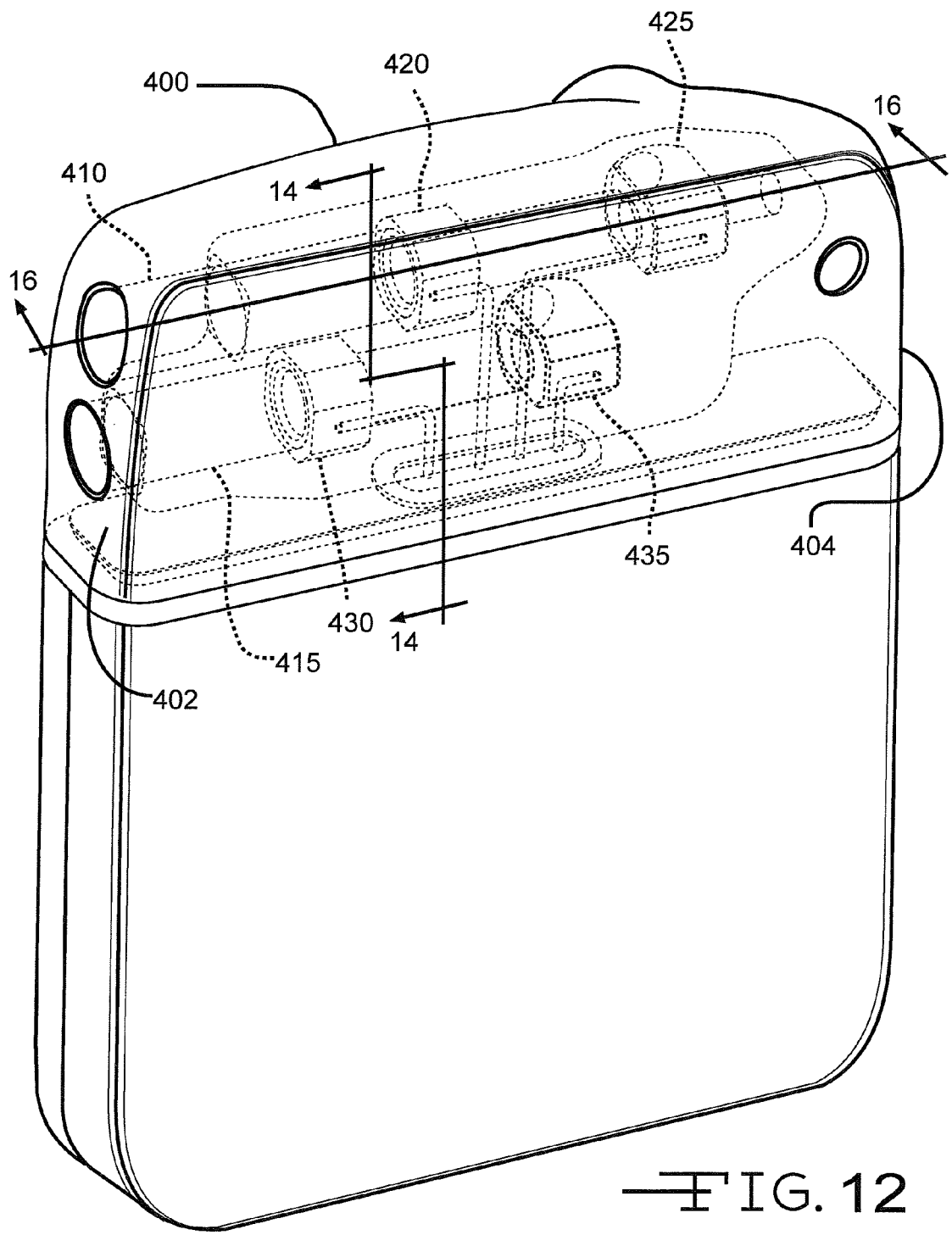
FIG. 12 is a perspective view of another embodiment of the header assembly of the present invention.
Figure 13:
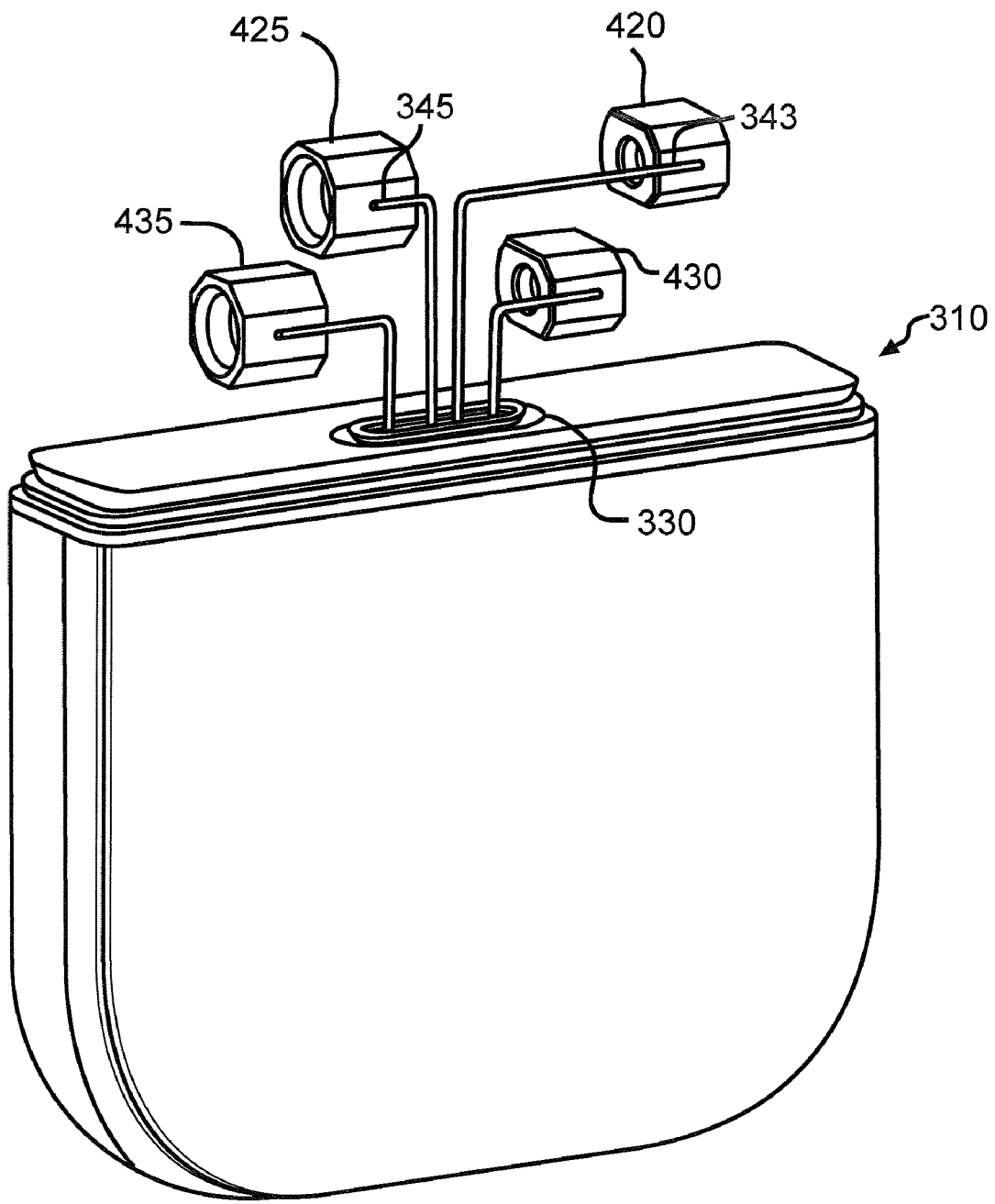
FIG. 13 is a perspective view of the base plate and feedthrough subassembly of the header assembly of FIG. 12, after the joining of terminal blocks to the ends of the wires of the feedthrough subassembly.

Alternatively, the four feedthrough wires may be divided and incorporated into separate feedthrough subassemblies. In one alternate embodiment, the four feedthrough wires are grouped as two wires provided in two feedthrough subassemblies. A preferred arrangement of the two-wire-by-two-feedthrough arrangement is depicted in FIGS. 12 and 13. Molded polymer body 400 of header assembly 300 encases a first conductive terminal 420 and a third conductive terminal 425 in a first coaxial relationship within a first bore 410. The polymeric body 400 also encases a second conductive terminal 430 and a fourth conductive terminal 435 in a second coaxial relationship within a second bore 415. The first and second terminals 420 and 430 are located toward the proximal end 402 of body 400, vertically above first a feedthrough subassembly 330. The third and fourth terminals 425 and 435 are located toward the distal end 404 of the body 400. In a similar manner as the previously described polymeric body 200 comprising first and second polymeric materials 198, 199, the body 400 is comprised of first and second polymeric materials, the latter molded over the former.

Figure 14:
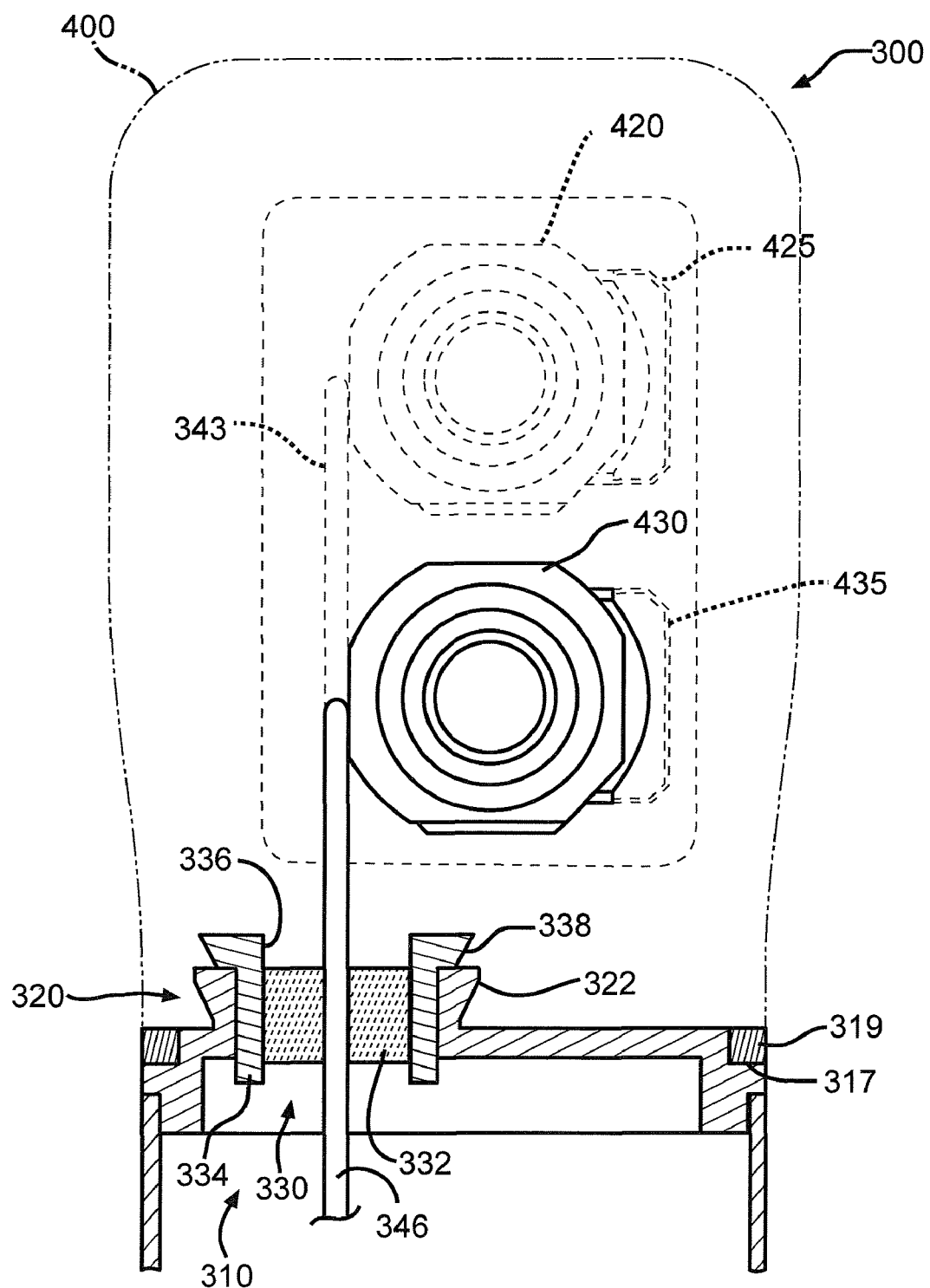
FIG. 14 is a cross-sectional view taken along the line 14-14 of FIG. 12.

The feedthrough subassembly 330 is shown in detail in FIGS. 12 to 14. The base plate 310 and feedthrough subassembly 330 are similar to the previously described base plate 110 and feedthrough subassemblies 130 and 130A of FIGS. 2 and 2A to 5. The base plate 310 is comprised of an upper region 320 including an overhang 322 that is preferably dovetail-shaped. The feedthrough subassembly 330 is disposed in a through hole in the base plate 310 and comprises a dovetail-shaped overhang 338 surrounding a tubular body 334 supporting a ceramic-to-metal seal 332 contained in an inner bore 336 thereof.

Alternatively, the feedthrough subassembly 330 may be formed integrally in the base plate 310 as described previously and depicted in FIG. 14.

Since the first and third conductive terminals 420, 430 are located vertically above the feedthrough subassembly 330, it is preferable that the feedthrough wires 342 and 346 contained therein are connected to terminals 420 and 430 as shown in FIGS. 12 and 13. In like manner, the feedthrough wires 344 and 348 are connected to terminals 425, 435. This arrangement is advantageous because it simplifies bending of the feedthrough wires 342, 344, 346 and 348 above the base plate 310 in order to route them to their respective terminals. Each of the feedthrough wires 342, 344, 346 and 348 has only a pair of bends that are coplanar to each other so that the respective distal ends of the wires are oriented vertically. A third bend in a substantially horizontal direction (as done for the distal ends 143, 145, 147 and 149 of wires 142, 144, 146 and 148 in FIG. 7) is not necessary. As a result, the feedthrough wire bending process is faster and more precise.

In a further embodiment, each of the conductive terminals is provided with a registration groove for receiving the distal end of its respective feedthrough wire. This is best understood with reference to FIGS. 16 and 16A. Referring first to FIG. 16, a bore 410 for receiving a conductive lead is formed in the header body 400. The conductive terminals 420 and 425 are partially encased in header body 400 with their lead-receiving openings 423 and 428 aligned in a coaxial relationship with the bore 410. A vertical outer wall 421 of the terminal 420 is provided with a vertical registration groove 422. A distal end 343 of the feedthrough wire 342 (FIG. 13) is disposed therein. In like manner, vertical outer wall 426 of terminal 425 is provided with a vertical registration groove 427 which receives the distal end 345 of feedthrough wire 344 (FIG. 13).

FIG. 16A depicts an exemplary connection between a conductive terminal 425 and the distal end 345 of the feedthrough wire 344. Connections between the other terminals and their respective feedthrough wires are similar. The radius of curvature and the vertical alignment of the registration groove 427 are made with high precision so that the terminal 425 is properly aligned with the feedthrough wire 344 with its opening 428 thereof positioned in a coaxial relationship with the opening 423 of its paired terminal 420. Additionally, this arrangement is advantageous because stronger and more precise parallel welds 429 can be made between a feedthrough wire and its terminal.

The header assemblies 100, 300 of FIGS. 8 and 12 are comprised of four feedthrough wires, two pairs of terminal blocks, and two conductor lead bores provided in the respective polymeric bodies. Those skilled in the art will understand that a header assembly according to the present invention can have more terminal blocks in addition to the two pairs shown. There can be three, four or more pairs. Additionally, it may be desired to have a header assembly where a bore only communicates with one terminal block which is not in a co-axial relationship with a second terminal block.

An optional additional step of sealing the molded polymer body to the base plate may also be performed. This is where a small bead of sealant is applied at the outer edge of the interface there between. Referring to FIG. 14, a step 317 provided in the base plate 310 forms a recess for receiving a bead of sealant. A seal 319 is formed in the recess by dispensing a suitable viscous liquid sealant (such as silicone rubber) therein, which cures into a solid seal.

After header assembly 100 is completely assembled as shown in FIG. 9, it may be joined to an implantable medical device and sealed to a casing containing the device. FIG. 10 is a perspective view of the header assembly 100 partially joined to a clamshell casing for the medical device. The first clam shell 24 comprises spaced apart side walls 36 and 38 extending to and meeting with a bottom wall 40. The side walls 36, 38 and the bottom wall 40 meet each other at rounded corners and extend to a back wall 42. Opposite the back wall 42 is a peripheral edge 44 of the side walls 36, 38 and the bottom wall 40. Opposite the bottom wall 40 is an open area.

The second clam shell 26 comprises spaced apart side walls 48 and 50 extending to and meeting with a bottom wall (not shown). The side walls 48 and 50 and bottom wall meet at rounded corners and extend to front wall 54. Opposite the front wall 54 is a peripheral edge 56 of the side walls 48 and 50 and bottom wall while opposite the bottom wall is an open area. The first clam shell 24 is sized to fit inside the periphery of the second clam shell 26 in a closely spaced, lap joint relationship. This assembly forms a container having an opening 60 leading therein when the clam shells 24 and 26 are joined to each other. The container opening 60 has a generally rectangular shape.

The benefit of having a lap joint construction for the mating clam shells 24, 26 is that when they are hermetically sealed together, such as by laser welding, the laser beam is prevented from compromising the control circuitry 12 and the power supply 14 of the medical device. With a coplanar or butted seam construction (not shown), it is possible for the laser beam to penetrate past the junction of the peripheral edges 44, 56 of the clam shells 24, 26 to compromise the internal device components or power supply housed therein. If a butt welded construction is used, a backing ring (not shown) is desired. An example of a backing ring for a butt weld construction is shown in U.S. Pat. No. 6,334,879 to Muffoletto et al., which is assigned to the assignee of the present invention and incorporated herein by reference.

In a preferred embodiment, the header assembly 100 is completely fabricated, including the feedthrough wires, conductive terminals, and molded polymer body 200 with the dovetail shaped overhang 122 encased therein. The implantable device is then positioned in close proximity beneath header assembly 100, and the proximal ends (not shown) of the feedthrough wires 142, 144, 146 and 148 are connected to the power supply, control circuitry, and other circuitry (not shown) of the medical device as required. It will be apparent that the feedthrough wires 142, 144, 146 and 148, including their proximal ends, may be longer than shown in the figures to facilitate connection to the medical device.

Next, the first clamshell 24 is mated to the base plate 110 with the upper edge 27 thereof in contact with the inverted step 117 (FIG. 3) and joined thereto by a weld 29 (FIG. 10). In like manner, the second clamshell 26 is mated to the base plate 110 with its upper edge 57 in contact with the inverted step 117 and joined thereto by a weld. So that implantable device 18 is hermetically sealed within the resulting casing 22, the peripheral edge 44 of clamshell 24 and the peripheral edge 56 of clamshell 26 are also joined to each other by welding.

Figure 11:
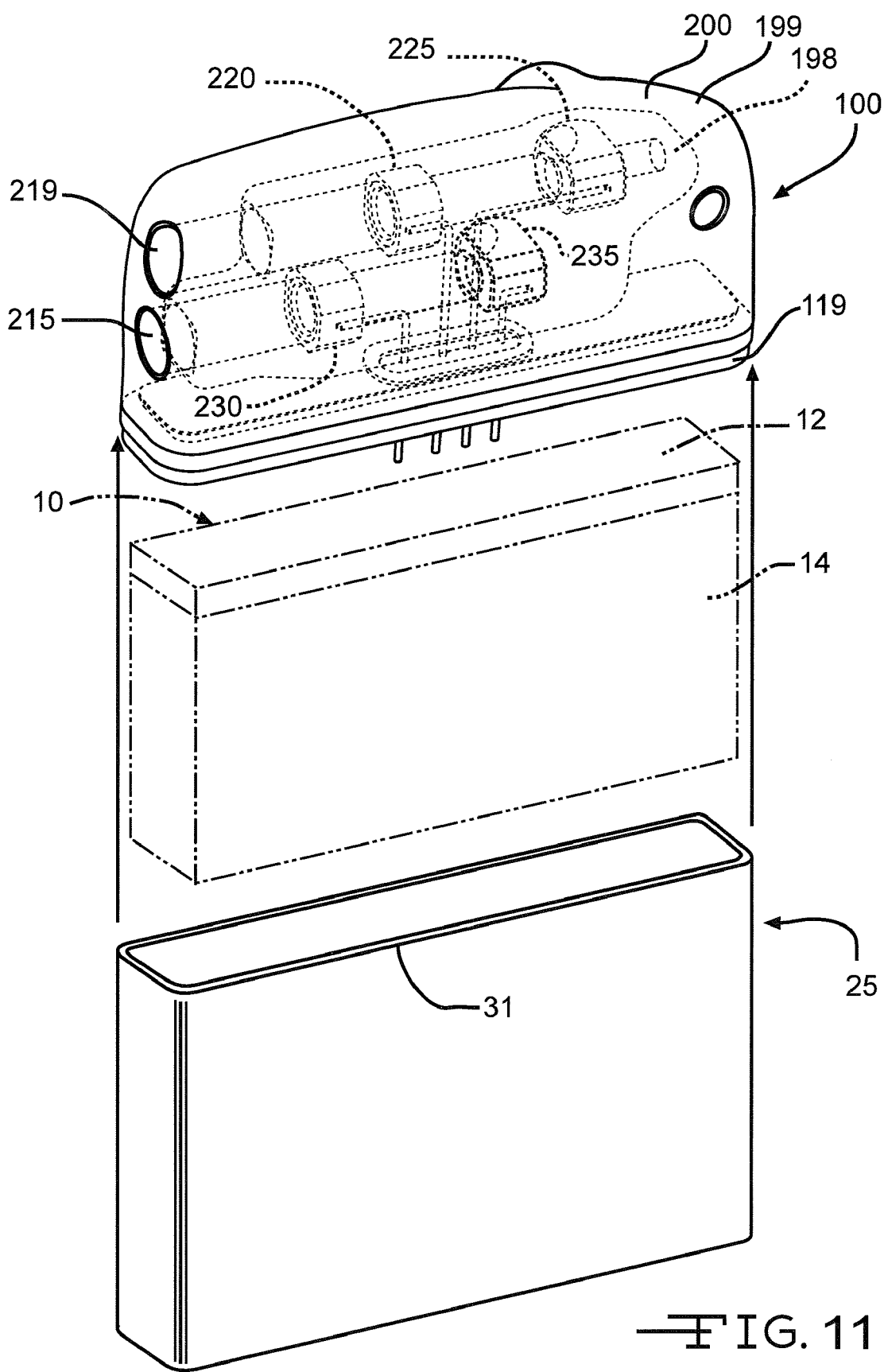
FIG. 11 is a perspective view of the header assembly of FIG. 9 prior to joining to a deep drawn device casing.

In another embodiment depicted in FIG. 11, a drawn device casing 25 is joined at its upper edge 31 thereof to the inverted step 117 of the base plate 110 by welding. While the medical device is shown contained inside a housing of mating clam shells 24, 26, or pf a drawn casing 25, the present invention is not intended to be so limited. Other types of housings such as those of a prismatic or cylindrical configuration are also contemplated.

It is, therefore, apparent that there has been provided, in accordance with the present invention, a header assembly for connecting a conductor terminating at a body organ with control circuitry and at least one electrical energy storage device of an implantable medical device. While this invention has been described in conjunction with preferred embodiments thereof, it is evident that many alternatives, modifications, and variations will be apparent to those skilled in the art. Accordingly, the disclosure is intended to embrace all such alternatives, modifications and variations that fall within the broad scope of the appended claims.

What is claimed is:

1. A header assembly for connecting a conductor terminating at a body organ with control circuitry and at least one electrical energy storage device of an implantable medical device, the header assembly comprising:
 a) a base plate comprising an upper surface, a lower surface, and a surrounding edge having a lower region and an upper region comprising an overhang having a lower perimeter and an upper perimeter, wherein the upper perimeter is greater than the lower perimeter;
 b) a first feedthrough subassembly disposed in a first through hole in the base plate, the first feedthrough subassembly comprising a first ceramic-to-metal seal formed within the first through hole, and at least a first feedthrough wire passing through the first ceramic-to-metal seal;
 c) at least a first electrically conductive terminal connected to a distal end of the first feedthrough wire and having a first lead opening sized to receive a first portion of a lead for the conductor;
 d) a body of polymeric material comprising a first polymeric material supporting the first terminal in a partially encased relationship and a second polymeric material encasing the first polymeric material and at least an upper region of the surrounding edge of the base plate so that the first terminal is prevented from moving in the header assembly; and
 e) a first bore communicating from outside the polymeric body to the first lead opening.

2. The header assembly of claim 1 further comprising a second electrically conductive terminal connected to a distal end of a second feedthrough wire passing through the first ceramic-to-metal seal and having a second lead opening sized to receive a second portion of the lead for the conductor.

3. The header assembly of claim 2 wherein the first and second lead openings are aligned in a first co-axial relationship.

4. The header assembly of claim 2 wherein the body of polymeric material further supports third and fourth electrically conductive terminals having third and fourth lead openings aligned in a second co-axial relationship along a second bore communicating from outside the body to the third and fourth terminals.

5. The header assembly of claim 4 wherein the first feedthrough subassembly further comprises a third feedthrough wire having a distal end connected to the third electrically conductive terminal and passing through the first ceramic-to-metal seal, and a fourth feedthrough wire having a distal end connected to the fourth electrically conductive terminal and passing through the first ceramic-to-metal seal.

6. The header assembly of claim 4 further comprising a second feedthrough subassembly disposed in a second through hole in the base plate, the second feedthrough subassembly comprising a second ceramic-to-metal seal formed within the second through hole, a third feedthrough wire having a distal end connected to the third electrically conductive terminal and passing through the second ceramic-to-metal seal, and a fourth feedthrough wire having a distal end connected to the fourth electrically conductive terminal and passing through the second ceramic-to-metal seal.

7. The header assembly of claim 6 wherein the second feedthrough subassembly further comprises a second tubular body having a main body perimeter, an inner bore containing the second ceramic-to-metal seal, and an upper end having an upper perimeter greater than the main body perimeter.

8. The header assembly of claim 7 wherein the upper end of the second tubular body is dovetail shaped.

9. The header assembly of claim 7 wherein the second tubular body further comprises a flange proximate the upper end thereof and engaged with the upper surface of the base plate.

10. The header assembly of claim 1 wherein the upper region of the surrounding edge of the base plate is dovetail shaped.

11. The header assembly of claim 10 wherein the body of polypolymeric material applies a constricting force on the dovetail shaped upper region of the surrounding edge of the base plate.

12. The header assembly of claim 1 wherein the first feedthrough subassembly further comprises a first tubular body having a main body perimeter, an inner bore containing the first ceramic-to-metal seal, and an upper end having an upper perimeter greater than the tubular main body perimeter.

13. The header assembly of claim 12 wherein the upper end of the first tubular body is dovetail shaped.

14. The header assembly of claim 12 wherein the first tubular body further comprises a flange proximate the upper end thereof and engaged with the upper surface of the base plate.

15. The header assembly of claim 12 wherein the first tubular body is joined to the base plate by welding.

16. The header assembly of claim 1 wherein the body of polymeric material comprises at least one of polyurethane and polysulfone.

17. The header assembly of claim 1 wherein the base plate is made of a material selected from stainless steel or titanium.

18. A header assembly for connecting at least first and second conductors terminating at a body organ with control circuitry and at least one electrical energy storage device of an implantable medical device, the header assembly comprising:
  a) a base plate comprising an upper surface, a lower surface, and a surrounding edge having a lower region and an upper region;
  b) a first feedthrough subassembly disposed in a first through hole in the base plate, the first feedthrough subassembly comprising a first ceramic-to-metal seal formed within the first through hole, and a first feedthrough wire and a second feedthrough wire passing through the first ceramic-to-metal seal;
  c) a second feedthrough subassembly disposed in a second through hole in the base plate, the second feedthrough subassembly comprising a second ceramic-to-metal seal formed within the second through hole, and a third feedthrough wire and a fourth feedthrough wire passing through the second ceramic-to-metal seal;
  d) a first electrically conductive terminal connected to a distal end of the first feedthrough wire and having a first lead opening sized to receive a first portion of a lead for the first conductor;
  e) a second electrically conductive terminal connected to a distal end of the second feedthrough wire and having a second lead opening sized to receive a first portion of the lead for the second conductor;
  f) a third electrically conductive terminal connected to a distal end of the third feedthrough wire and having a third lead opening sized to receive a second portion of the lead for the first conductor;
  g) a fourth electrically conductive terminal connected to a distal end of the fourth feedthrough wire and having a fourth lead opening sized to receive a second portion of the lead for the second conductor;
  h) a body of polymeric material comprising a first polymeric material supporting the first, second, third and fourth terminals in a partially encased relationship and a second polymeric material encasing the first polymeric material and at least the upper region of the surrounding edge of the base plate so that the terminals are prevented from moving in the header assembly;
  i) a first bore communicating from outside the polymeric body to the first and third lead openings aligned in a first co-axial relationship; and
  j) a second bore communicating from outside the polymeric body to the second and fourth lead openings aligned in a second co-axial relationship.

19. The header assembly of claim 18 wherein the distal ends of the first, second, third, and fourth feedthrough wires are aligned substantially perpendicular to the first, second, third, and fourth lead openings of the first, second, third, and fourth electrically conductive terminals, respectively.

20. The header assembly of claim 19 wherein at least the distal end of the first feedthrough wire is aligned with and disposed in a groove formed in the first terminal.

21. The header assembly of claim 18 wherein the upper region of the surrounding edge of the base plate comprises an overhang having a lower perimeter and an upper perimeter, and wherein the upper perimeter is greater than the lower perimeter.

22. The header assembly of claim 18 wherein the upper region of the surrounding edge of the base plate is dovetail shaped.

23. The header assembly of claim 18 wherein the first feedthrough subassembly further comprises a first tubular body having a first inner bore containing the first ceramic-to-metal seal and the second feedthrough subassembly further comprises a second tubular body having a second inner bore containing the second ceramic-to-metal seal.

24. The header assembly of claim 23 wherein the first tubular body of the first feedthrough subassembly has a first main body perimeter, and a first upper end with a first upper perimeter greater than the first main body perimeter, and the second tubular body of the second feedthrough subassembly has a second main body perimeter, and a second upper end with a second upper perimeter greater than the second tubular main body perimeter.

25. The header assembly of claim 24 wherein upper ends of the first and second tubular bodies are dovetail shaped.

26. The header assembly of claim 24 wherein the first tubular body further comprises a first flange proximate the upper end thereof and engaged with the upper surface of the base plate, and the second tubular body further comprises a second flange proximate the upper end thereof and engaged with the upper surface of the base plate.

27. The header assembly of claim 24 wherein the first and second tubular bodies are joined to the base plate by welding.

28. The header assembly of claim 18 wherein the body of polymeric material comprises at least one of polyurethane and polysulfone.

29. The header assembly of claim 18 wherein the base plate is made of a material selected from stainless steel or titanium.

30. An implantable device comprising:
 a) a casing;
 b) at least one electrical energy storage device powering control circuitry contained in the casing; and
 c) a header assembly comprising:
  i) a base plate comprising an upper surface, a lower surface, and a surrounding edge having a lower region and an upper region comprising an overhang having a lower perimeter and an upper perimeter, wherein the upper perimeter is greater than the lower perimeter;
  ii) a first feedthrough subassembly disposed in a first through hole in the base plate, the first feedthrough subassembly comprising a first ceramic-to-metal seal formed within the first through hole, and at least a first feedthrough wire passing through the first ceramic-to-metal seal;
  iii) at least a first electrically conductive terminal connected to a distal end of the first feedthrough wire and having a first lead opening sized to receive a first portion of a lead for the conductor;
  iv) a body of polymeric material comprising a first polymeric material supporting the first terminal in a partially encased relationship and a second polymeric material encasing the first polymeric material and at least an upper region of the surrounding edge of the base plate so that the first terminal is prevented from moving in the header assembly; and
  v) a first bore communicating from outside the polymeric body to the first lead opening.

31. A header assembly for connecting a conductor terminating at a body organ with control circuitry and at least one electrical energy storage device of an implantable medical device, the header assembly comprising:
 a) a base plate comprising an upper surface, a lower surface, and a surrounding edge having a lower region and an upper region comprising an overhang having a lower perimeter and an upper perimeter, wherein the upper region of the surrounding edge of the base plate is dovetail shaped such that the upper perimeter of the base plate is greater than the lower perimeter thereof;
 b) a first feedthrough subassembly disposed in a first through hole in the base plate, the first feedthrough subassembly comprising a first ceramic-to-metal seal formed within the first through hole, and at least a first feedthrough wire passing through the first ceramic-to-metal seal;
 c) at least a first electrically conductive terminal connected to a distal end of the first feedthrough wire and having a first lead opening sized to receive a first portion of a lead for the conductor;
 d) a body of polymeric material encasing at least an upper region of the surrounding edge of the base plate and supporting the first terminal in a partially encased relationship so that the first terminal is prevented from moving in the header assembly; and
 e) a first bore communicating from outside the polymeric body to the first lead opening.

32. The header assembly of claim 31 wherein the body of polymeric material applies a constricting force on the dovetail shaped upper region of the surrounding edge of the base plate.

33. A header assembly for connecting a conductor terminating at a body organ with control circuitry and at least one electrical energy storage device of an implantable medical device, the header assembly comprising:
 a) a base plate comprising an upper surface, a lower surface, and a surrounding edge having a lower region and an upper region comprising an overhang having a lower perimeter and an upper perimeter, wherein the upper perimeter is greater than the lower perimeter;
 b) a first feedthrough subassembly disposed in a first through hole in the base plate, the first feedthrough subassembly comprising a first ceramic-to-metal seal formed within the first through hole, and at least a first feedthrough wire passing through the first ceramic-to-metal seal, wherein the first feedthrough subassembly further comprises an inner bore containing the first ceramic-to-metal seal, and a first tubular body comprising a main body perimeter with an upper end thereof having a dovetail shape such that an upper perimeter of the first tubular body is greater than the tubular main body perimeter;
 c) at least a first electrically conductive terminal connected to a distal end of the first feedthrough wire and having a first lead opening sized to receive a first portion of a lead for the conductor;
 d) a body of polymeric material encasing at least an upper region of the surrounding edge of the base plate and supporting the first terminal in a partially encased relationship so that the first terminal is prevented from moving in the header assembly; and
 e) a first bore communicating from outside the polymeric body to the first lead opening.

34. The header assembly of claim 33 wherein the first tubular body further comprises a flange proximate the upper end thereof and engaged with the upper surface of the base plate.

35. A header assembly for connecting a conductor terminating at a body organ with control circuitry and at least one electrical energy storage device of an implantable medical device, the header assembly comprising:
 a) a base plate comprising an upper surface, a lower surface, and a surrounding edge having a lower region and an upper region comprising an overhang having a lower perimeter and an upper perimeter, wherein the upper perimeter is greater than the lower perimeter;
 b) a first feedthrough subassembly disposed in a first through hole in the base plate, the first feedthrough subassembly comprising a first ceramic-to-metal seal formed within the first through hole, and at least a first feedthrough wire passing through the first ceramic-to-metal seal;
 c) at least a first electrically conductive terminal comprising a groove in which a distal end of the first feedthrough wire resides connected to the first terminal having a first lead opening sized to receive a first portion of a lead for the conductor;
 d) a body of polymeric material encasing at least an upper region of the surrounding edge of the base plate and supporting the first terminal in a partially encased relationship so that the first terminal is prevented from moving in the header assembly; and
 e) a first bore communicating from outside the polymeric body to the first lead opening.

36. An implantable device comprising:
a) a casing;
b) at least one electrical energy storage device powering control circuitry contained in the casing; and
c) a header assembly comprising:
  i) a base plate comprising an upper surface, a lower surface, and a surrounding edge having a lower region and an upper region comprising an overhang having a lower perimeter and an upper perimeter, wherein the upper region of the surrounding edge of the base plate is dovetail shaped such that the upper perimeter is greater than the lower perimeter thereof;
  ii) a first feedthrough subassembly disposed in a first through hole in the base plate, the first feedthrough subassembly comprising a first ceramic-to-metal seal formed within the first through hole, and at least a first feedthrough wire passing through the first ceramic-to-metal seal;
  iii) at least a first electrically conductive terminal connected to a distal end of the first feedthrough wire and having a first lead opening sized to receive a first portion of a lead for the conductor;
  iv) a body of polymeric material encasing at least an upper region of the surrounding edge of the base plate and supporting the first terminal in a partially encased relationship so that the first terminal is prevented from moving by the polymeric material; and
  v) a first bore communicating from outside the polymeric body to the first lead opening.

37. The implantable device of claim 36 wherein the body of polymeric material applies a constricting force on the dovetail shaped upper region of the surrounding edge of the base plate.

38. An implantable device comprising:
a) a casing;
b) at least one electrical energy storage device powering control circuitry contained in the casing; and
c) a header assembly comprising:
  i) a base plate comprising an upper surface, a lower surface, and a surrounding edge having a lower region and an upper region comprising an overhang having a lower perimeter and an upper perimeter, wherein the upper perimeter is greater than the lower perimeter;
  ii) a first feedthrough subassembly disposed in a first through hole in the base plate, the first feedthrough subassembly comprising a first ceramic-to-metal seal formed within the first through hole, and at least a first feedthrough wire passing through the first ceramic-to-metal seal, wherein the first feedthrough subassembly further comprises an inner bore containing the first ceramic-to-metal seal, and a first tubular body comprising a main body perimeter with an upper end thereof having a dovetail shape such that an upper perimeter of the first tubular body is greater than the tubular main body perimeter;
  iii) at least a first electrically conductive terminal connected to a distal end of the first feedthrough wire and having a first lead opening sized to receive a first portion of a lead for the conductor;
  iv) a body of polymeric material encasing at least an upper region of the surrounding edge of the base plate and supporting the first terminal in a partially encased relationship so that the first terminal is prevented from moving by the polymeric material; and
  v) a first bore communicating from outside the polymeric body to the first lead opening.

* * * * *